United States Patent
Termanini

(10) Patent No.: US 8,845,743 B2
(45) Date of Patent: *Sep. 30, 2014

(54) INTERLOCKING REVERSE SHOULDER PROSTHESIS METHOD

(71) Applicant: Hip Innovation Technology LLC, Plantation, FL (US)

(72) Inventor: Zafer Termanini, Boca Raton, FL (US)

(73) Assignee: Hip Innovation Technology, LLC, West Orange, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/650,397

(22) Filed: Oct. 12, 2012

(65) Prior Publication Data

US 2014/0128982 A1    May 8, 2014

Related U.S. Application Data

(63) Continuation of application No. 12/799,609, filed on Apr. 28, 2010, now Pat. No. 8,313,531.

(60) Provisional application No. 61/339,680, filed on Mar. 8, 2010.

(51) Int. Cl.
*A61F 2/40* (2006.01)
*A61F 2/30* (2006.01)

(52) U.S. Cl.
CPC ........... *A61F 2/40* (2013.01); *A61F 2002/4022* (2013.01); *A61F 2002/4085* (2013.01); *A61F 2002/30649* (2013.01); *A61F 2002/30247* (2013.01); *A61F 2002/4011* (2013.01); *A61F 2002/30332* (2013.01); *A61F 2002/4033* (2013.01); *A61F 2002/30784* (2013.01); *Y10S 623/908* (2013.01)
USPC ....................... 623/19.13; 623/19.12; 623/908

(58) Field of Classification Search
USPC ..................... 623/19.11–19.14, 22.11–22.14, 623/22.4–22.46, 23.11–23.14, 23.39–23.43
See application file for complete search history.

(56) References Cited

U.S. PATENT DOCUMENTS

| 3,506,982 A | 4/1970 | Steffee |
| 3,837,008 A | 9/1974 | Bahler et al. |

(Continued)

FOREIGN PATENT DOCUMENTS

| EP | 0 322 493 B1 | 8/1991 |
| EP | 1 508 315 A2 | 2/2005 |

(Continued)

OTHER PUBLICATIONS

International Search Report dated May 9, 2011 from US International Searching Authority.

(Continued)

*Primary Examiner* — Marcia Watkins
(74) *Attorney, Agent, or Firm* — Norris McLaughlin & Marcus, P.A.

(57) ABSTRACT

An interlocking reverse shoulder prosthesis including a glenoid cup being implanted in the glenoid fossa having a glenoid ball, firmly attached to the central portion of the cup via Morse taper. The humeral component having a hemispherical cup attached to the neck of the implant via Morse taper in a modular fashion thereby allowing use of several neck lengths. After implantation of the glenoid cup, glenoid hall and the humeral cup, the members are assembled together for relative movement. The glenoid cup is secured by several screws or resorbable fixation studs. During range of motion, the edge of the humeral cup becomes inserted into a gap located between the glenoid cup and the glenoid ball and becomes restrained thus reducing the likelihood of dislocation during extreme range of motion.

9 Claims, 4 Drawing Sheets

(56) References Cited

U.S. PATENT DOCUMENTS

| | | | |
|---|---|---|---|
| 3,868,730 A | 3/1975 | Kaufer et al. | |
| 3,916,451 A | 11/1975 | Buechel et al. | |
| 3,978,528 A | 9/1976 | Crep | |
| 4,030,143 A | 6/1977 | Elloy et al. | |
| 4,206,517 A | 6/1980 | Pappas et al. | |
| 4,693,723 A | 9/1987 | Gabard | |
| 4,792,337 A | 12/1988 | Müller | |
| 4,846,840 A | 7/1989 | Leclercq et al. | |
| 5,092,898 A | 3/1992 | Bekki et al. | |
| 5,462,563 A | 10/1995 | Shearer et al. | |
| 6,010,535 A | 1/2000 | Shah | |
| 6,527,808 B1 | 3/2003 | Albertorio et al. | |
| 6,749,637 B1 | 6/2004 | Bäehler | |
| 6,790,234 B1 | 9/2004 | Frankle | |
| 6,800,095 B1 | 10/2004 | Pope et al. | |
| 7,011,686 B2 | 3/2006 | Ball et al. | |
| 7,033,396 B2 | 4/2006 | Tornier | |
| 7,169,184 B2 | 1/2007 | Pria | |
| 7,175,663 B1 | 2/2007 | Stone | |
| 7,241,314 B1 | 7/2007 | Winslow | |
| 7,309,360 B2 | 12/2007 | Tornier et al. | |
| 7,462,197 B2 | 12/2008 | Tornier et al. | |
| 7,465,319 B2 | 12/2008 | Tornier | |
| 7,470,287 B2 | 12/2008 | Tornier | |
| 7,611,539 B2 | 11/2009 | Bouttens et al. | |
| 7,854,768 B2 | 12/2010 | Wiley et al. | |
| 8,313,531 B2 * | 11/2012 | Termanini | 623/22.15 |
| 8,540,779 B2 * | 9/2013 | Termanini | 623/22.15 |
| 2002/0143402 A1 | 10/2002 | Steinberg | |
| 2002/0173853 A1 | 11/2002 | Corl, III et al. | |
| 2003/0114934 A1 | 6/2003 | Steinberg | |
| 2003/0120347 A1 | 6/2003 | Steinberg | |
| 2004/0039449 A1 | 2/2004 | Tornier | |
| 2004/0220673 A1 | 11/2004 | Pria | |
| 2005/0165490 A1 | 7/2005 | Tornier | |
| 2005/0288791 A1 | 12/2005 | Tornier et al. | |
| 2006/0069443 A1 | 3/2006 | Deffenbaugh et al. | |
| 2008/0154369 A1 | 6/2008 | Barr et al. | |
| 2009/0112328 A1 | 4/2009 | Tornier et al. | |
| 2009/0113238 A1 | 4/2009 | Liu et al. | |
| 2009/0192621 A1 | 7/2009 | Winslow | |
| 2009/0287309 A1 | 11/2009 | Walch et al. | |
| 2010/0131073 A1 | 5/2010 | Meridew et al. | |
| 2010/0222886 A1 | 9/2010 | Wiley et al. | |
| 2011/0054628 A1 | 3/2011 | Banks et al. | |
| 2011/0151259 A1 | 6/2011 | Jarman-Smith et al. | |
| 2011/0218637 A1 | 9/2011 | Termanini | |
| 2011/0218638 A1 | 9/2011 | Termanini | |
| 2011/0218645 A1 | 9/2011 | Garcia Saban et al. | |
| 2011/0230590 A1 | 9/2011 | Jarman-Smith et al. | |
| 2012/0116533 A1 | 5/2012 | Forsell | |

FOREIGN PATENT DOCUMENTS

| | | |
|---|---|---|
| EP | 1 543 801 B1 | 8/2007 |
| FR | 2603476 A1 | 3/1988 |
| FR | 2841768 A1 | 1/2004 |
| JP | 1175846 A | 7/1989 |
| JP | 200473854 A | 3/2004 |
| JP | 2005177496 A | 7/2005 |
| TW | 2011/12996 A1 | 4/2011 |
| WO | WO9710776 A3 | 3/1997 |
| WO | WO2011/006852 A1 | 1/2011 |

OTHER PUBLICATIONS

A. Roth, K. Sander, F. Layher, J. Babisch, R. Venbrocks; "In vivo measurement of polyethylene wear in cementless total hip arthroplasty"; Acta Chir Orthop Traumatol Cech. Feb. 2010;77(1):13-7; Clinic of Orthopaedics, Rudolf-Elle Hospital, Department of Orthopoaedics of the Friedrich-Schiller University of Jena, Eisenberg, Germany; ajroth@gmx.de.

G. Schmidig, A. Patel, I. Kiepins, M. Thakore, DC Markel; "The effects of acetabular shell deformation and liner thickness on frictional torque in ultrahigh-molecular-weight polyethylene acetabular bearings"; J. Arthroplasty, Jun. 2010: 25(4):64453. Epub Jun. 2, 2009; Stryker Orthopaedics. Mahway, New Jersey, USA.

H. Ito, A. Minami T. Matsuno, H. Tanino, T. Yuhta, I. Nishimura; "The sphericity of the bearing surface in total hip arthroplasty"; J. Arthroplasty, Dec. 2001;16(8):1024-9; Department of Orthopaedic Surgery, Hokkaido University, School of Medicine, Sapporo, Japan; itobiro@med.hokudaiac.jp.

P. Hernigou, T. Bahrami; "Zirconia and alumina ceramics in comparison with stainless-steel heads. Polyethylene wear after a minimum ten-year follow-up"; J Bone Joint Surg. Br. May 2003;85(4):504-9.

D. Dowson, ZM Jin; Metal-on-metal hip joint tribology; Proc Inst Mech Eng H. Feb. 2006;220(2):107-18.

Chen, Cheng-Fong; Chen, Wei-Ming; Yang, Chan-Tsung; Huang,Ching-Kuei; Chen, Tain-Hsiung; Hybrid Assembly of Metal Head and Femoral Stem From Manufacturers During Isolated Acetabular Revision;Artificial Organs, vol. 34, Issue 8, pp. E242-E245; Publ. Aug. 2010.

Beldame, J.; Carreras, F.; Oger, P.; Beaufils, P.; Cementless cups do not increase osteolysis risk in metal-on-metal total hip arthroplasty; Orthopaedics & Traumatology-Surgery & Research, vol. 95, Issue 7, pp. 478-490. Publ. Nov. 2009, Elsevier Masson SAS.

Pavelka, T; Linhart, M; Houcek. P.; [Hip joint arthroplasty following surgical treatment of acetabular fracture]—Aloplastika kycelniho kloubu po operacnim leceni zlomenin acetabula; Acta chirurgiae orthopaedicae et traumatologiae Cechoslovaca. vol. 73, Issue 4, pp. 268-274; Publ. Aug. 2006.

Hamadouche, M; Madi, F.; Kerboull, L.; Courpied, Jr.; Kerboull, M.; Early femoral osteolysis following CharnleyKerboull total hip arthroplsty combining a 22-mm zirconia head on polyethylene; Revue De Chirurgie Orthopedique et Reparatrice De l Appareil Moteur, vol. 91, Issue 5, pp. 439-445, Publ. Sep. 2005, Elsevier SAS.

Bal, BS; Vandelune, D.; Gurba, DM; Jasty, M.; Harris WH; Polyethylene wear in cases using femoral stems of similar geometry, but different metals, porous layer, and modularity; Journal of Arthroplasty, vol. 13, Issue 5, pp. 492-499; Publ. Aug. 1998.

Schreurs, B. Willem; Van Tienen, TonyG.; Buma, Pieter; Verdonschot, Nico; Gardeniers, Jean WM; Slooff, Tom JJH; Favorable results of acetabular reconstruction with impacted morsellised bone grafts in patients younger than 50 years: A 10- to 18-year follow-up study of 34 cemented total hip arthroplasties; Journal: Acta orthopaedica Scandinavica, 72 (2), 120-126; Publ. 2001, INIST-CNRS.

Supplementary European Search Report, Apr. 9, 2013.

U.S. Appl. No. 61/339,680, filed Mar. 8, 2010, Termanini.

U.S. Appl. No. 13/895,712, filed May 16, 2013, Termanini.

U.S. Appl. No. 13/933,474, filed Jul. 2, 2013, Termanini.

* cited by examiner

INTERLOCKING REVERSE SHOULDER PROSTHESIS METHOD

CROSS REFERENCE TO RELATED APPLICATIONS

This application claims the benefit of U.S. Provisional Patent Application Ser. No. 61/339,680 filed on Mar. 8, 2010 and entitled "INTERLOCKING REVERSE HIP PROSTHESIS," and U.S. Pat. No. 8,313,531 B2 entitled "INTERLOCKING REVERSE HIP PROSTHESIS AND METHOD" the entirety of both of which are incorporated herein by reference.

BACKGROUND OF THE INVENTION

1. Field of the Invention

The present invention relates generally to hip prostheses and more specifically to an interlocking reverse hip prosthesis allowing increased range of motion and stability during excessive ranges of motion.

2. Description of the Prior Art

It can be appreciated that several hip implants have been in use for years. Typically, a conventional hip implant comprises a femoral component having an articulating femoral ball attached to a stem, which is inserted into the medullary canal of the femur after preparation and reaming using appropriate reamers by the operating surgeon. Said stem can be secured with bone cement or press fit. An acetabular component or socket having the shape of a cup is inserted into the acetabular cavity after preparation and appropriate reaming and secured with cancellous screws through holes in the implant, bone cement or press fit or combination of thereof.

The acetabular cup will then receive a lining made of high-density polyethylene or ceramic. Said lining will be secured into the acetabular shell by a press fit mechanism. The main problem with conventional hip implants is the instability of the prosthesis at extreme ranges of motion thereby allowing the femoral ball to dislodge and dislocate. Prior art teaches constrained and preassembled ball and socket devices or a device wherein the ball and socket members are implanted separately whereupon the ball element is forced into a resilient opening in the socket and thereafter held in place by the resilient material. Other constrained acetabular sockets include a locking ring such as the one described by Albertorio et al. U.S. Pat. No. 6,527,808. In the case of socket elements having a retaining ring, the ball member is forcefully inserted into the socket after the two elements are implanted. This constitutes a weak link where forces exerted on the prosthesis by ambulatory motion may exceed the forces used to assemble the implant thereby causing the ball to be separated from the socket.

While these devices may be suitable for the particular purpose to which they address, they are not suitable for providing an interlocking mechanism as in the reverse hip implant design of the present invention, which by the very nature of its design allows increased range of motion and increased stability at extreme ranges of motion thereby reducing the risk of dislocation.

In these respects, the interlocking reverse hip prosthesis according to the present invention substantially departs from the conventional concept and design of the prior art, and in so doing provides an apparatus primarily developed for the purpose of reducing the risk of dislocation of hip implants at extreme ranges of motion. Furthermore, since the articulating surfaces of the two components are fully in contact 100% of the time, it is clear that this will improve the weight distribution and decrease the wear of the surfaces in contact and reduce the number of wear particles released in the joint. The later, being very detrimental to the proper function of the joint.

BRIEF DESCRIPTION OF THE DRAWINGS

Various other objects, features and advantages of the present invention will become fully appreciated as the same becomes better understood when considered in conjunction with the current accompanying drawings, in which like reference characters designate the same or similar elements throughout the several views, and wherein.

SUMMARY OF THE INVENTION

Figure 1:
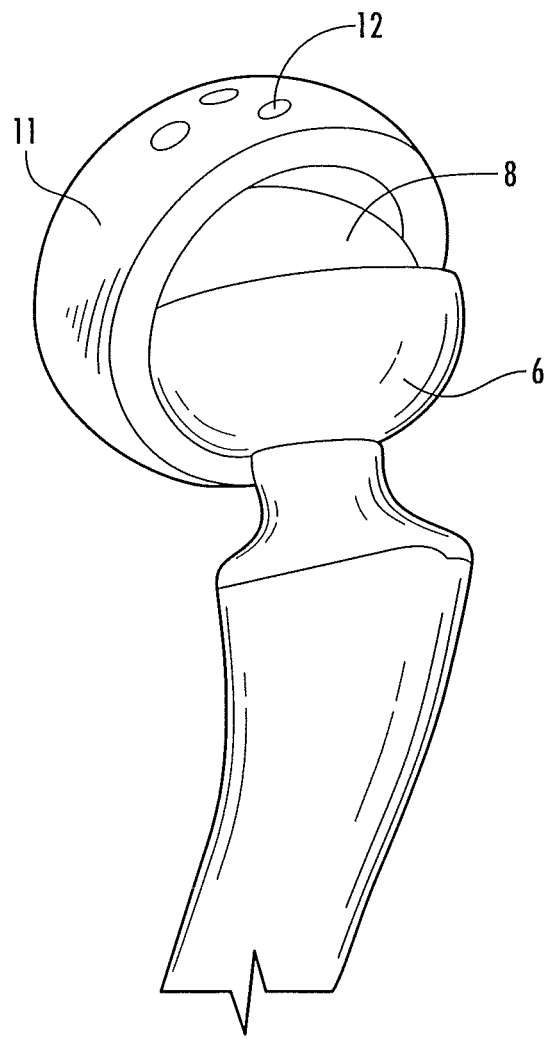
FIG. 1 is a perspective view of the interlocking reverse hip prosthesis.
Figure 2:
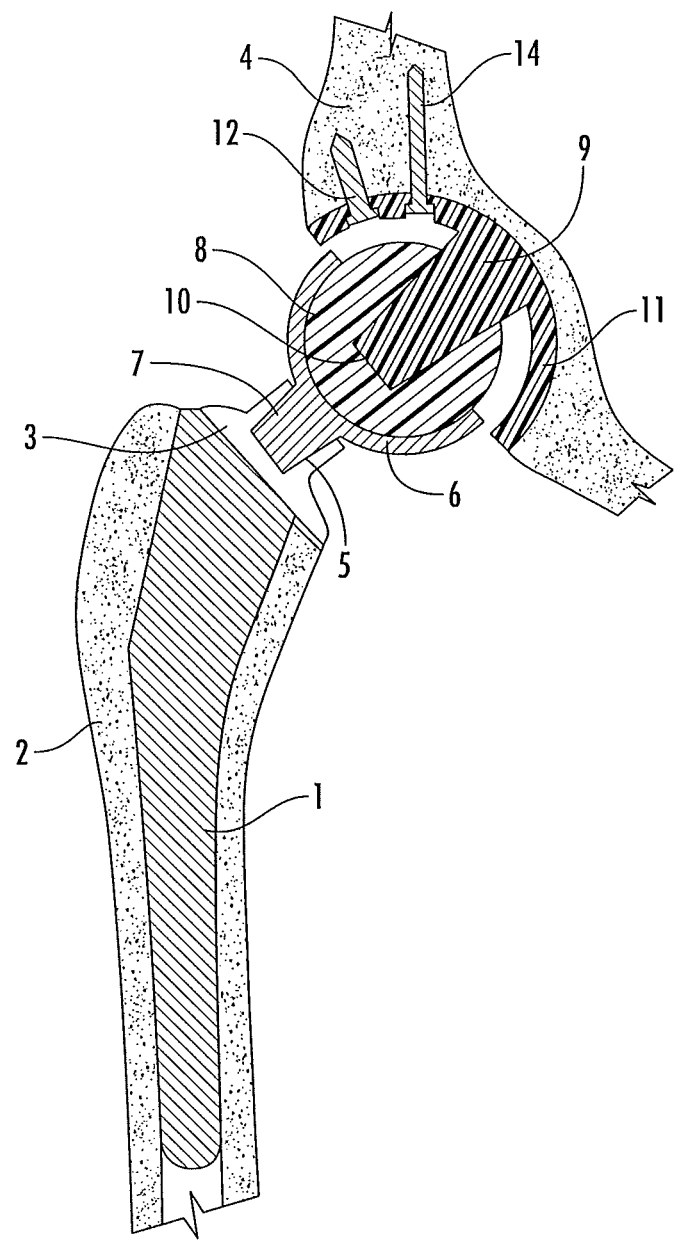
FIG. 2 is a sectional view of the interlocking reverse hip prosthesis.
Figure 3:
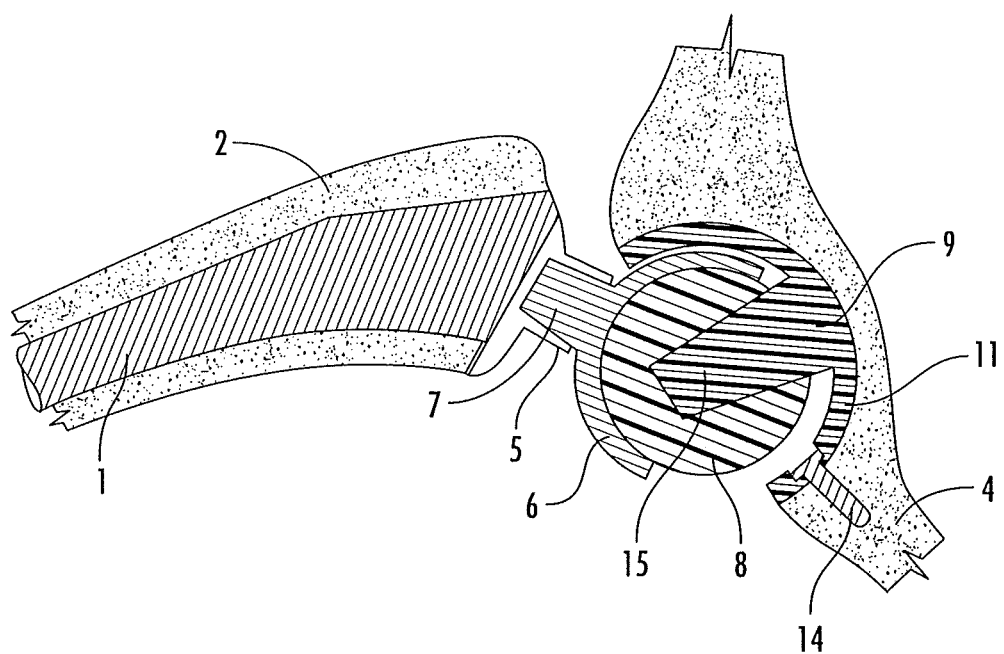
FIG. 3 is a sectional view of the interlocking reverse hip prosthesis in extension and external rotation.
Figure 4:
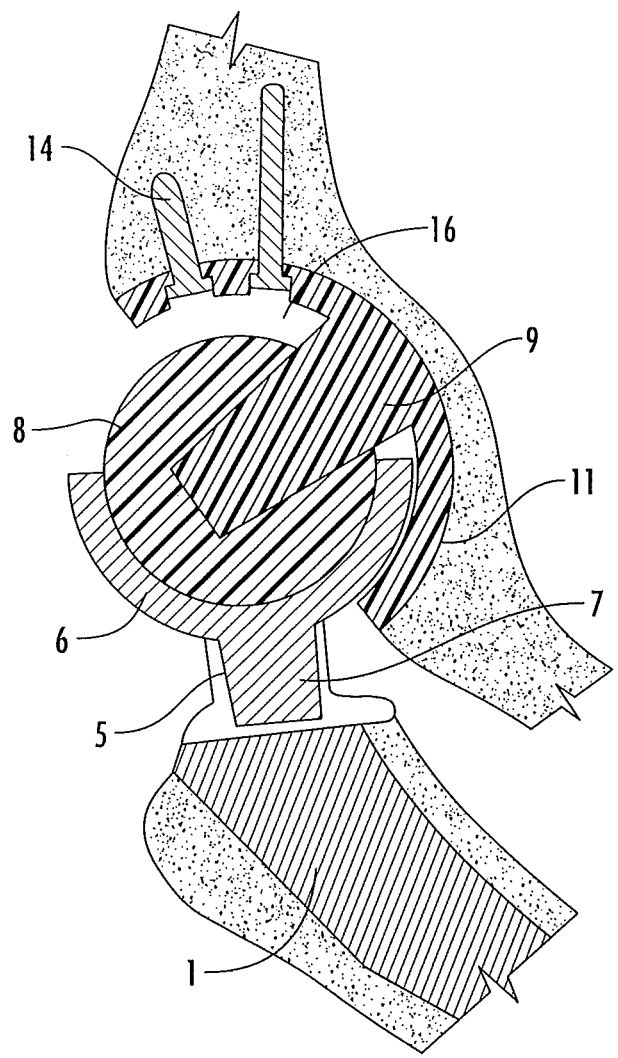
FIG. 4 is a sectional view of the interlocking reverse hip prosthesis in flexion and internal rotation.

The present invention provides a new interlocking reverse hip prosthesis construction wherein an articulating acetabular ball member of the acetabular component is solidly and concentrically attached to a central protrusion or stem of an acetabular cup via Morse taper. A hemispherical femoral cup member is solidly attached to the femoral stem via Morse taper. Said acetabular cup or socket is implanted in an acetabular opening or cavity constructed by the surgeon into the pelvic bone to which it is firmly secured by one or more screws through one or more openings in the acetabular cup. In another embodiment of this invention the screws can be replaced by biocompatible resorbable studs of variable number. The femoral stem is then inserted and impacted into the femoral medullary canal which has been prepared and hollowed by the surgeon using appropriate reamers. The femoral hemispherical articulating cup is then firmly attached to the proximal end of the femoral stem via Morse Taper. Subsequently, the hip is reduced and the femoral and acetabular components are put in contact whereby the femoral hemispherical articulating cup will concentrically glide over the acetabular ball. During ambulation, the femoral cup edge or lip will glide conformably into a hemispherical gap (16) located between the acetabular ball and the acetabular cup. Furthermore, by its very geometrical configuration, it becomes very difficult for the femoral cup to dislocate when the range of motion increases since it becomes constrained in the hemispherical locking space between the acetabular cup and the acetabular ball.

Furthermore, since the articulating surfaces of the two components are fully in contact 100% of the time, it is clear that this will improve the weight distribution and decrease the wear of the surfaces in contact and reduce the number of wear particles released in the joint.

There has thus been outlined, rather broadly, the more important features of the invention in order that the detailed description may be better understood, and in order that the present contribution to the art may be better appreciated. The novel feature of this invention, whereby the location of the articulating surfaces of the hip joint, namely the ball and socket, is reversed, resulting in a new restrained reverse hip prosthesis which is not anticipated, rendered obvious, suggested or even implied by any prior conventional hip prosthesis, either alone or in any combination thereof.

In this respect, before explaining at least one embodiment of the invention in detail, it is to be understood that the invention is not committed in its application to the details of construction and the arrangements of the component set forth in the following description or illustrated in the drawings. The invention is capable of other embodiments and of being practiced and carried out in various ways. Also, it is to be understood that the terminology employed herein are for the purpose of the description and should not be regarded as limiting.

To the accomplishment of the above and related objects, this invention may be embodied in the form illustrated in the accompanying drawings. Attention being called to the fact, however, that the drawings are elicited only, and that changes may be made to any specific construction illustrated.

DETAILED DESCRIPTION OF THE ENABLING EMBODIMENTS

Turning now descriptively to the drawings, in which similar reference characters denote similar elements throughout the several views, the attached figures illustrate an interlocking reversed hip prosthesis, which comprises a hemispherical acetabular cup (11) having a smooth concave surface and a convex non-articulating surface. The convex non-articulating surface provides a porous surface with multiple asperities and micro-voids to allow bone ingrowth. Furthermore, the acetabular cup (11) provides one or more holes (12) at different locations for the purpose of using one or more screws (14). In another embodiment, the screws (14) can be replaced with resorbable nonmetallic and biocompatible studs of different diameter and length. These orthobiologic resorbable studs will secure the acetabular cup (11) during the initial phase of bone ingrowth and will resorb within one year, being replaced by newly generated bone and become part of the host bone. During that period, the acetabular cup (11) is by then solidly attached to the acetabular bone by bone ingrowth. The concave hemispherical surface of the acetabular cup (11) provides a large interior cylindrical protrusion or stem (9), which has a male Morse taper (15) for assembly to the female Morse taper (10) of the acetabular ball (8). The hemispherical articulating femoral cup (6) has a central cylindrical protrusion (7) on its convex surface, which has a male Morse taper for assembly to a recess (5) with female Morse taper located at the shoulder (3) of the femoral stem (1). The central protrusion (7) of the femoral cup (6) comes in different lengths thereby allowing use of several neck lengths in a modular fashion.

In another embodiment of the invention, the articulating femoral cup (6) will have a female Morse taper while the femoral stem (1) would have a male Morse taper.

An important advantage of the present invention is that the greater the interdigitation the more stability of the implant as opposed to the conventional femoral ball and socket hip implants, where increased range of motion is usually associated with increased risk of dislocation.

During the implantation of the prosthesis of the present invention, the operating surgeon will initially prepare the proximal femoral bone (2) by using conventional reamers in the usual fashion. The acetabular cavity in the pelvic bone (4) is reamed to the appropriate size to accept the acetabular cup (11), which is impacted for press fit at the right angle of inclination and orientation. Fixation screws or biocompatible resorbable studs are then inserted in place to secure the acetabular cup (11). The femoral stem (1) is then inserted into the femoral canal and can be cemented or press fit. The acetabular ball (8) is then inserted onto the central protrusion or stem (9) of the acetabular cup (11). Subsequently, the articulating femoral cup (6) is inserted onto the proximal femoral stem via Morse taper (5). Once the insertion of the components is complete, the implant is assembled together.

In one embodiment, the articulating surface of the femoral cup contains a high molecular weight polyethylene lining of varying thickness, but no less than 4 mm. In a different embodiment the lining could be porcelain or other metallic alloy.

Another embodiment is directed to prosthesis for a shoulder joint. The first component includes an anchoring glenoid plate or glenoid cup firmly attached to the concave surface of the glenoid fossa. The glenoid cup having a glenoid cup stem and a glenoid ball firmly affixed thereto. The second component being a hemispherical humeral cup having a stem like protrusion, which is firmly attached via Morse taper to a humeral stem to be inserted into the medullary canal of the proximal humerus.

It is therefore the object of the present invention to provide a new and improved interlocking and restrained reverse hip prosthesis system, where the conventional articulating surfaces of the hip joint are reversed and interlocked. The system described in the present invention has all the advantages of the prior art of known design and configuration and none of the disadvantages.

With respect to the above description then, it is to be realized that the optimum dimensional relationships for the parts of the invention, to include variations in size, material, shape, form, function and manner of operation, assembly and use, are deemed readily apparent and obvious to one skilled in the art, and all equivalent relationships to those illustrated in the drawings and described in the specification are intended to be encompassed by the present invention. Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A method of implanting in a patient a reverse shoulder prosthesis, the method comprising: providing the prosthesis comprising a unitary glenoid cup having an outer non-articulating surface adapted for attachment to a glenoid fossa and a concave surface located opposite to the non-articulating surface, the concave surface having a glenoid cup stem firmly affixed therein and projecting outwardly therefrom, a glenoid ball firmly affixed to the glenoid cup stem, the glenoid ball having a surface, the concave surface of the glenoid cup and the surface of the glenoid ball are spaced from one another, thereby defining a gap therebetween, a humeral stem adapted for implantation in a medullary canal of a proximal end of a humerus, and a humeral cup firmly affixed to a proximal end of the humeral stem, the humeral cup sized for articulation in the gap, such that the humeral cup has a concave surface sized for articulation on the surface of the glenoid ball and a convex surface opposite the concave surface of the humeral cup sized for articulation on the concave surface of the glenoid cup, the gap being sized and configured to permit said articulations while constraining the humeral cup within the gap throughout an entire range of said articulations of the humeral cup as it articulates within the gap, thereby reducing the risk of dislocation;

preparing a glenoid fossa and affixing the glenoid cup therein, preparing a medullary canal at the proximal end of a humerus and affixing the humeral stem therein, affixing the glenoid ball to the glenoid cup stem, affixing the humeral cup to the proximal end of the humeral stem and aligning the concave surface of the humeral cup with the glenoid ball so that the humeral cup will articulate in the gap and the concave surface of the humeral cup will articulate on the surface of the glenoid ball.

2. The method of claim 1 wherein the concave surface of the glenoid cup is hemispherical, the glenoid ball is spherical and the concave surface of the humeral cup is hemispherical.

3. The method of claim 1 wherein the concave surface of the glenoid cup has a center and the glenoid cup stem is affixed thereto and in the center.

4. The method of claim 1 wherein the glenoid ball has a glenoid ball recess sized to receive the glenoid cup stem.

5. The method of claim 4 wherein the glenoid ball has a center, the glenoid cup stem has a longitudinal center line and the glenoid ball recess has a longitudinal center line, both longitudinal center lines being colinear and passing through the center of the glenoid ball.

6. The method of claim 1 wherein the humeral cup has a humeral cup stem projecting outwardly therefrom in a direction opposite the concave surface thereof and the humeral stem has at its proximal end a recess sized to receive the humeral cup stem.

7. The method of claim 6 wherein the humeral cup has a concave hemispherical portion having a center line, the humeral cup stem has a longitudinal center line and the humeral stem recess has a longitudinal center line wherein all of the center lines are colinear.

8. The method of claim 1 wherein the concave surface of the humeral cup is fully in contact with the surface of the glenoid ball during articulation of said concave surface on the glenoid ball.

9. The method of claim 1 wherein the gap is hemispherical.

* * * * *